US010975201B2

(12) United States Patent
Boday et al.

(10) Patent No.: US 10,975,201 B2
(45) Date of Patent: *Apr. 13, 2021

(54) SYSTEMS CHEMISTRY APPROACH TO POLYHEXAHYDROTRIAZINE POLYMERIC STRUCTURES

(71) Applicant: International Business Machines Corporation, Armonk, NY (US)

(72) Inventors: Dylan J. Boday, Tucson, AZ (US); Mareva B. Fevre, San Jose, CA (US); Jeannette M. Garcia, San Leandro, CA (US); James L. Hedrick, Pleasanton, CA (US); Rudy J. Wojtecki, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 146 days.

This patent is subject to a terminal disclaimer.

(21) Appl. No.: 16/156,606

(22) Filed: Oct. 10, 2018

(65) Prior Publication Data

US 2019/0040200 A1   Feb. 7, 2019

Related U.S. Application Data

(62) Division of application No. 15/460,785, filed on Mar. 16, 2017, now Pat. No. 10,118,993, which is a division of application No. 14/951,186, filed on Nov. 24, 2015, now Pat. No. 9,873,766.

(51) Int. Cl.

| | |
|---|---|
| *C08G 73/06* | (2006.01) |
| *C07D 207/452* | (2006.01) |
| *C08L 79/04* | (2006.01) |
| *C08L 63/04* | (2006.01) |
| *C08G 73/10* | (2006.01) |
| *C08L 63/00* | (2006.01) |

(52) U.S. Cl.
CPC ..... *C08G 73/0644* (2013.01); *C07D 207/452* (2013.01); *C08G 73/065* (2013.01); *C08G 73/1039* (2013.01); *C08G 73/1064* (2013.01); *C08G 73/1067* (2013.01); *C08L 63/00* (2013.01); *C08L 63/04* (2013.01); *C08L 79/04* (2013.01); *H05K 999/99* (2013.01)

(58) Field of Classification Search
CPC .. C08L 63/00–10; C08L 79/08; C08L 79/085; C08L 81/06; C08L 81/10
See application file for complete search history.

(56) References Cited

U.S. PATENT DOCUMENTS

| | | |
|---|---|---|
| 2,889,277 A | 6/1959 | Hughes |
| 3,340,232 A | 9/1967 | Smith et al. |
| 3,598,748 A | 8/1971 | Hirosawa |
| 3,957,742 A | 5/1976 | Kveton |
| 3,969,300 A | 7/1976 | Nagata et al. |
| 4,003,864 A | 1/1977 | Roth et al. |
| 4,106,904 A | 8/1978 | Oude Alink et al. |
| 4,160,754 A | 7/1979 | Schapel et al. |
| 4,224,417 A | 9/1980 | Hajek et al. |
| 4,225,481 A | 9/1980 | Wagner |
| 4,246,160 A | 1/1981 | Wagner et al. |
| 4,301,262 A | 11/1981 | Wagner et al. |
| 4,877,451 A | 10/1989 | Winnik et al. |
| 5,002,830 A | 3/1991 | Gillis et al. |
| 5,010,144 A | 4/1991 | Phanstiel, IV et al. |
| 5,089,567 A | 2/1992 | Phanstiel et al. |
| 5,112,796 A | 5/1992 | Iannicelli |
| 5,210,191 A | 5/1993 | Phanstiel et al. |
| 5,674,377 A | 10/1997 | Sullivan, III et al. |
| 5,830,243 A | 11/1998 | Wolak et al. |
| 7,384,434 B2 | 6/2008 | Malfer et al. |
| 8,841,134 B2 | 9/2014 | Papineni et al. |
| 8,907,049 B2 | 12/2014 | Baidak et al. |
| 8,980,278 B2 | 3/2015 | Steinberg et al. |
| 8,980,295 B2 | 3/2015 | Kao et al. |
| 9,587,108 B2 | 3/2017 | Boday et al. |
| 9,758,620 B2 | 9/2017 | Boday et al. |
| 9,873,766 B2 | 1/2018 | Boday et al. |
| 9,957,345 B2 | 5/2018 | Boday et al. |
| 10,023,735 B2 | 7/2018 | Boday et al. |
| 10,118,993 B2 * | 11/2018 | Boday .................. H05K 999/99 |
| 2004/0048782 A1 | 3/2004 | Bryson |
| 2004/0209987 A1 | 10/2004 | Gajiwala |
| 2005/0089744 A1 | 4/2005 | Kim et al. |
| 2007/0031498 A1 | 2/2007 | Zong et al. |

(Continued)

FOREIGN PATENT DOCUMENTS

| | | |
|---|---|---|
| CN | 101265255 A | 9/2008 |
| EP | 2636697 A1 | 9/2013 |

(Continued)

OTHER PUBLICATIONS

IBM, "List of IBM Patents or Patent Applications Treated as Related," for U.S. Appl. No. 16/156,606, filed Oct. 10, 2018, titled "Systems Chemistry Approach to Polyhexahydrotriazine Polymeric Structures".

Henri Ulrich et al Reaction of Chloromethyl Ether with Primary Amines, May 1961, pp. 1637-1638.

Wang Yulan et al., Synthesis and Properties of Poly-1, 3, 5-Triazines, Polymer Communications, No. 2, 1984, 99. 117-123.

John Markoff, Error at IBM Lap Finds New Family of Materials, New York Times, May 15, 2014, 4 pages.

Jeanette M. Garcia et al., Recyclable, Strong Thermosets and Organogels via Paraformaldehyde Condensation with Diamines, Science AAAS, vol. 344, May 16, 2014, pp. 732-735.

(Continued)

Primary Examiner — Ana L. Woodward
(74) Attorney, Agent, or Firm — Patterson + Sheridan, LLP

(57) ABSTRACT

In some embodiments, a product, such as a thermoset, has a polyhexahydrotriazine and a self-polymerized cross-linkable polymer. In some embodiments, a product is the reaction product of a diamine, an aldehyde, and a compound having an $\alpha,\beta$-unsaturated electron withdrawing moiety.

16 Claims, 2 Drawing Sheets

(56) References Cited

U.S. PATENT DOCUMENTS

| | | |
|---|---|---|
| 2008/0014438 A1 | 1/2008 | Ruhle et al. |
| 2009/0039018 A1 | 2/2009 | Jordi et al. |
| 2010/0107476 A1 | 5/2010 | Cosimbescu |
| 2011/0114493 A1 | 5/2011 | Macnamara et al. |
| 2012/0049308 A1 | 3/2012 | Nishimura et al. |
| 2013/0204010 A1 | 8/2013 | Grinstaff et al. |
| 2014/0058047 A1 | 2/2014 | Grinstaff et al. |
| 2015/0084232 A1 | 3/2015 | Rutz et al. |
| 2015/0104579 A1 | 4/2015 | Hedrick et al. |
| 2015/0148488 A1 | 5/2015 | Greger et al. |
| 2017/0183451 A1 | 6/2017 | Boday et al. |

FOREIGN PATENT DOCUMENTS

| | | |
|---|---|---|
| GB | 928112 A | 6/1963 |
| GB | 1531578 A | 11/1978 |
| WO | 0166614 A2 | 9/2001 |
| WO | 0198388 A1 | 12/2001 |
| WO | 0226849 A1 | 4/2002 |

OTHER PUBLICATIONS

Farrar, "Reactions of Formaldehyde With Aromatic Amines," J. Appl. Chem. 14, 1964, 389-399.

Hiller, et al., "Laser-engravable hexahydrotriazine polymer networks," Materials Research Innovations, Oct. 2002, vol. 6, Issue 4, 179-184 [Abstract Only].

Oliver, et al., "Measurement of hardness and elastic modules by; instrumented indentiation: Advances in understanding and; refinements to methodolgy," J. Mater. Res., vol. 19, No. 1, Jan. 2004, 3-20.

Singh, et al., "Ultrasond mediated Green Synthesis of Hexa-hydro Triazines," J. Mater. Environ. Sci. 2 (4) (2011) 403-406.

M. Hofmann., 3D Printing Gets a Boost and Opportunites with Polymer Materials, ACS MacroLetters, 2014, 382-286.

K. Sun et al. "3D Printing of Interdigitated Li-lin Microbattery Architectures," Advanced Materials, 2013, 5 pages.

Fox et al, "Supramolecular Motifs in Dynamic Covalent PEG-Hemiaminal Organogels," Nature Communications, Jul. 15, 2015, 9 pages.

Hemant S. Patel et al., Studies on Synthesis and Characterization of some Novel Aromatic Copolyesters based on s-Triazine, Iranian Polymer Journal, vol. 14, No. 12, 2005, pp. 1090-1098.

Fabino Suriano et al., Functionalizied cyclic carbonates: from synthesis and metal-free catalyzed ring-opening polymerization to applications, Polymer Chemistry, The Royal Society of Chemistry, 2011, Accpeted Aug. 3, 2019, pp. 528-533.

D.R. Anderson et al., Thermally resistance polymers containing the s-triazine ring, Journal of Polymer Science Part A-1: Polymer Chemistry, vol. 4, Issue 7, pp. 1689-1702. [Abstract Only].

T. Okita, Filter method for the determination of trace quantities of amines, mercaptans, and organic sulphides in the atmosphere, Atmospheric Environment (1967), vol. 4, Issue 1, Jan. 1970, pp. 93-102.

Raquel Lebrero et al., Oder abatement in biotrickling filters: Effect of the EBRT or methyl mercaptan and hydrophobic VOCS removal, Bioresouce Technology, Special Issue: Innovative Researches on Algal Biomass, vol. 109, Apr. 2012, pp. 38-45.

Elbert et al."Conjugate Addition Reactions Combined with Free-Radical Cross-Linking for the Design of Materials for Tissue Engineering," Biomacromolecules 201, 2, 430-441; Published on Web Mar. 3, 2001.

Geng, et al., "Nanoindentation behavior of ultrathin polymeric films," Polymer 46 (2005) 11768-11772; Available online Oct. 19, 2005.

Stafford, et al., "A buckling-based metrology for measuring; the elastic moduli of polymeric thin films," Nature Materials. sub.—Aug. 3, 2004, 545-550;Published online: Jul. 11, 2004.

* cited by examiner

Graph 1: DSC scans (vs. maleimide content of the film)

Graph 2: DSC scans (vs. polyimide content of the film)

SYSTEMS CHEMISTRY APPROACH TO POLYHEXAHYDROTRIAZINE POLYMERIC STRUCTURES

CROSS-REFERENCE TO RELATED APPLICATIONS

This application is a divisional application of U.S. application Ser. No. 15/460,785 filed Mar. 16, 2017, which is a divisional of U.S. application Ser. No. 14/951,186 filed Nov. 24, 2015, now U.S. Pat. No. 9,873,766. The above-mentioned applications are hereby incorporated by reference.

FIELD

Embodiments herein generally relate to polyhexahydrotriazines (PHTs) with tailored macromolecular architectures.

BACKGROUND

Polyhexahydrotriazines (PHTs) are an emerging class of high strength engineering thermosetting polymers (thermosets) that have a unique combination of properties. PHTs have high modulus, solvent resistance, and resistance to environmental stress cracking. The ability to tune both the thermal and mechanical properties of PHTs is critical to meet the increasingly stringent demands of structural materials. Addition of a second polymer to a PHT network is one method of tuning the thermal or mechanical properties of a PHT network, but such multicomponent PHT networks suffer from biphasic separation of the individual polymers and multistep syntheses are required in order to obtain each type of polymer for the PHT network.

Therefore, there is a need in the art for PHT networks and multicomponent PHT networks with improved material properties, and improved syntheses of these networks.

SUMMARY

In some embodiments, a product has a polyhexahydrotriazine and a self-polymerized cross-linked polymer.

In some embodiments, a product is the reaction product of a diamine, an aldehyde, and a compound having an α,β-unsaturated electron withdrawing moiety.

DETAILED DESCRIPTION

Figure 1:
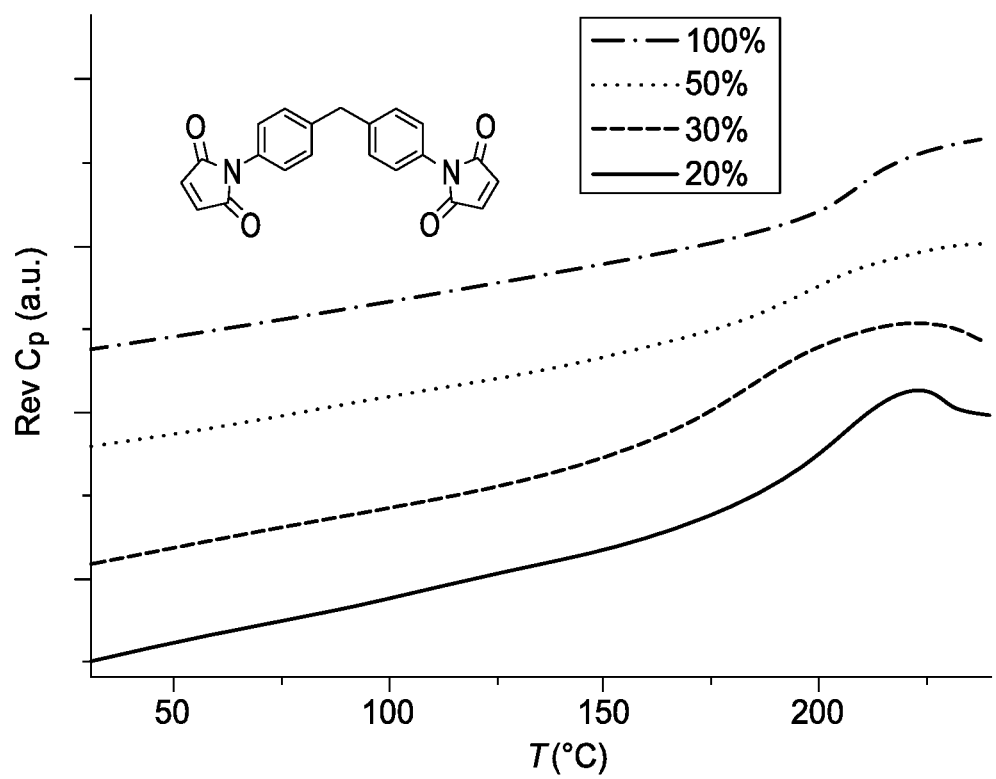
FIG. 1 is a graph illustrating relative glass transitions (reversing heat capacity) obtained after curing the films at 200° C.

Embodiments herein generally relate to polyhexahydrotriazines (PHTs) with tailored macromolecular architectures. New PHT materials with tailored macromolecular architectures and their methods of preparation are disclosed. In particular, the new PHT materials may serve as a thermoset for polymer pre-impregnated mat (pre-preg) and for lightweight and high strength composites in the fields of electronics, automotive, and aerospace. To that end, a systems chemistry approach may be used to synthesize PHT materials that achieve tunable material properties such as yield strength, char yield, and thermal response. A systems chemistry approach allows for access to tunable properties through the directed application of isolated and/or interrelated chemical reactions, simultaneously in a single vessel. The chemical reactions described herein may, however, also be performed individually in separate vessels, where products, which may be thermosets, are then formed by mixing (and optionally curing) the isolated polymer reaction products. Nonetheless, in the context of PHT materials, a systems chemistry approach allows mitigation of some of the challenges for recyclable high-performance thermosetting hexahydrotriazines conveniently by incorporating functional groups that promote the desired material properties in a single step through judicious choice of polymers and/or co-polymers based on reactivity.

In some embodiments, a thermoset has a polyhexahydrotriazine and a self-polymerized cross-linked polymer. The self-polymerized cross-linked polymer may be selected from polycyanate, polyalkyne, and polyimide. In some embodiments, the product further comprises a poly(amine-imide) copolymer. As described herein, the term 'copolymer' includes a polymer derived from more than one species of monomer. The poly(amine-imide) copolymer may be of the structure:

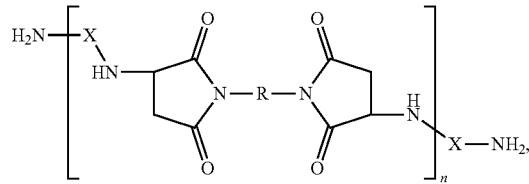

where R is selected from the group consisting of ether, aryl, and alkyl, X is a phosphine derivative, ether, or lactone. The length of polymers described herein is limited to the polymerization of monomers and/or viscosity of reaction mixtures (vitrification). The present disclosure is meant to cover all such polymers. Typically, n is a positive integer, such as from between about 2 to about 500, such as between about 2 and about 100, such as between about 10 and about 50. In some embodiments, the product further comprises a copolymer having a conjugate addition product, such as a Michael-adduct, and a hexahydrotriazine moiety. The product may further comprise a self-polymerized compound, polymerized from a compound having an α,β-unsaturated electron withdrawing moiety (i.e., an acceptor), such as a Michael acceptor. As used herein, the term "acceptor" means a compound having an α,β-unsaturated electron withdrawing moiety. The self-polymerized acceptor may be of the formula:

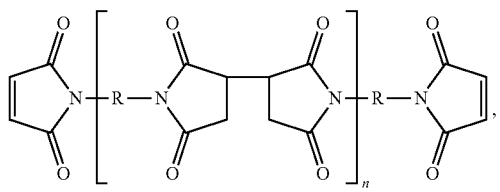

where R is ether, aryl, or alkyl, and n is a positive integer, such as from between about 2 to about 500, such as between about 2 and about 100, such as between about 10 and about 50. In some embodiments, the product further comprises a copolymer having a self-polymerized compound formed by an α,β-unsaturated electron withdrawing moiety before polymerization, such as a Michael acceptor, and an amino reacted adduct of a compound having an α,β-unsaturated electron withdrawing moiety before, such as a Michael adduct. The product may also have a cross-linked copolymer. In some embodiments, the product has a poly(amino-alcohol).

In some embodiments, a product is the reaction product of a diamine, an aldehyde, and a compound having an α,β-unsaturated electron withdrawing moiety. The aldehyde may be a polyaldehyde that is paraformaldehyde. The product may have a cross-linkable polymer. The cross-linkable polymer may be functionalized with at least one of cyanate, alkyne, epoxide, maleimide, and norbornene-2,3-dicarboximide. The cross-linkable polymer may be selected from the group consisting of:

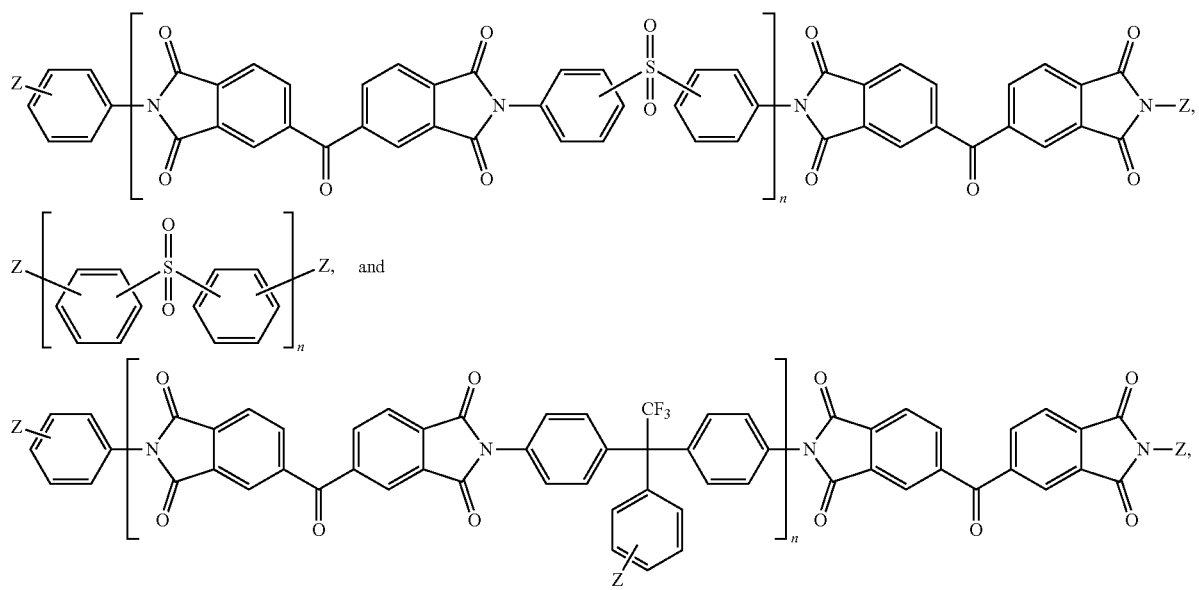

where each instance of 'Z' is independently selected from maleimide, norbornene-2,3-dicarboximide, cyanate, alkyne, and epoxide. The maleimide group, the norbornene-2,3-dicarboximide, the cyanate, the alkyne, and the epoxide may be unsubstituted or substituted with alkyl or aryl. Aryl includes phenyl, napthyl, anthracenyl, and pyrenyl. Aryl includes one or more C1-C20 alkyl moieties covalently bonded to one or more C6-C20 aryl moieties. Alkyl includes C1-C20 alkyl, such as C1-C6 alkyl. 'n' may be a positive integer, such as from between about 2 to about 500, such as between about 2 and about 100, such as between about 10 and about 50. Maleimide may be of the structure:

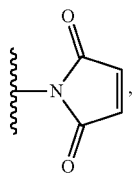

norbornene-2,3-dicarboximide may be of the structure:

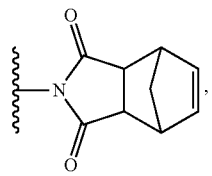 [SMILES: *N1C(=O)C2C3C=CC(C3)C2C1=O]

cyanate may be of the structure:

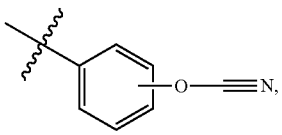

alkyne may be of the structure:

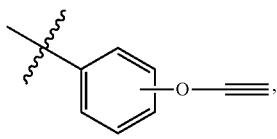

and epoxide may be of the structure:

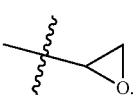

In some embodiments, the acceptor of the product is of the structure:

where R is selected from the group consisting of ether, aryl, and alkyl. Ether may be of the structure:

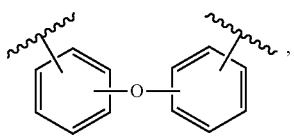

aryl may be of the structure:

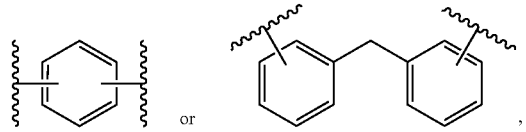

and alkyl may be of the structure:

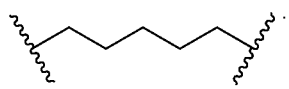 [SMILES: *CCCCC*]

In some embodiments, the diamine of the product is of the structure: $NH_2$—X—$NH_2$, where X is a phosphine derivative, ether, or lactone. The phosphine derivative may be

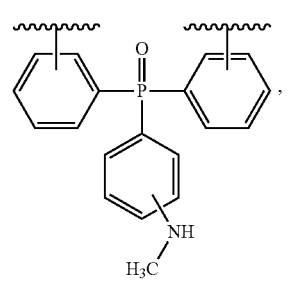

the ether may be of the structure:

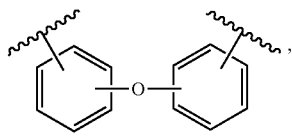

and the lactone may be of the structure:

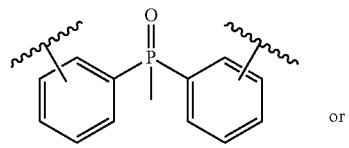

In some embodiments, a reaction mixture comprises compounds that react to form a PHT. In some embodiments, the α-terminus and/or ω-terminus of a diamine reacts with an aldehyde to form an imine intermediate, and the imine intermediate then forms a hexahydrotriazine linkage upon reaction of the imine intermediate with two other imine intermediates present in the reaction mixture, as shown in Scheme 1. As described herein, an α-terminus and ω-terminus refer to opposing ends of a molecule or polymer. The reaction of Scheme 1 is typically performed at a temperature above 50° C., such as about 200° C., to form the PHT.

Scheme 1

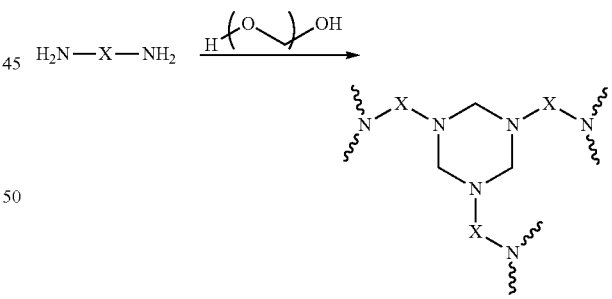

Each instance of 'X' independently includes a phosphine derivative, ether, and lactone. In some embodiments, a phosphine derivative is selected from the general structures:

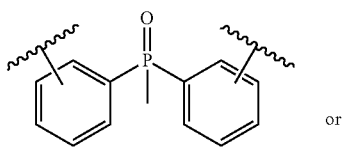

or

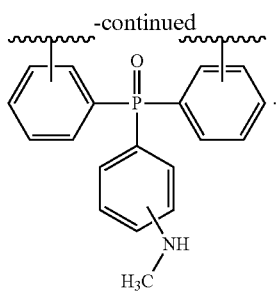

Ether includes arylethers and alkylethers. An arylether may be of the general structure:

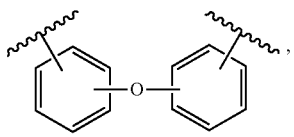

such that the diamine is, for example, 4,4'-oxydianiline (ODA).

Lactone includes aryl substituted lactones and alkyl substituted lactones. In some embodiments, a lactone is a phthalide of the general structure:

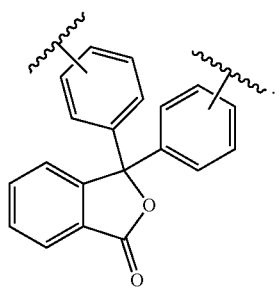

Diamine monomers, and other reactive monomers described herein, may serve as reactive diluent(s) for polymerization reactions allowing for solution processing of oligomers and polymers described herein. Furthermore, oligomers and polymers described herein having —NH$_2$ moieties at the α- and/or ω-termini may also react at the α- and/or ω-termini with paraformaldehyde to form an imine capable of forming a hexahydrotriazine linkage. A different carbonyl containing compound (i.e., not paraformaldehyde) may be used in addition to or as a replacement of paraformaldehyde. Carbonyl containing compounds include aldehydes and ketones. As described herein, the term "aldehyde" includes aldehyde monomers and aldehyde monomers that can polymerize to form polyethers, such as paraformaldehyde. Paraformaldehyde may be added to a reaction mixture, where it can decompose in situ into formaldehyde monomers (which have carbonyl moieties). Decomposition of paraformaldehyde may be promoted by heating the reaction mixture. Aldehydes include formaldehyde, acetaldehyde, and polymerized aldehydes such as paraformaldehyde. A ketone, such as acetone, may be used instead of or in addition to an aldehyde.

Conjugate addition is a reaction between a nucleophile (a donor) and an activated olefin or alkyne functionality (a compound having an α,β-unsaturated electron withdrawing moiety, i.e. an "acceptor"), where the nucleophile covalently bonds to a carbon of the activated olefin or alkyne. An olefin or alkyne is considered 'activated' if the olefin or alkyne is located adjacent to an electron withdrawing group such as a carbonyl moiety. One way to describe an activated olefin or alkyne is a "compound having an α,β-unsaturated electron withdrawing moiety." Electron withdrawing moieties include carbonyl, nitro, nitrile, and aryl. In the context of Michael addition, the Michael addition nucleophile is known as a "Michael donor" and the activated electrophilic olefin or alkyne is known as a "Michael acceptor". In some embodiments, a reaction mixture comprises an α,β-unsaturated electron withdrawing moiety and/or a diamine. In some embodiments, the α-terminus and/or ω-terminus of a diamine is a nucleophile and reacts with compound containing an α,β-unsaturated electron withdrawing moiety to form a diamine-acceptor adduct. Acceptors include acrylates and maleimides of the general structure (1):

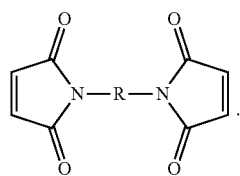

(1)

Acrylate includes diacrylates and triacrylates, such as 1,4-butanediol diacrylate and trimethylolpropane triacrylate, respectively. 'R' includes ethers, aryl, and alkyl. Ether includes arylethers and alkylethers. In some embodiments, ether is of the general structure

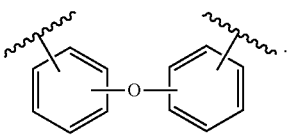

Aryl includes phenyl, napthyl, anthracenyl, and pyrenyl. In some embodiments, aryl is of the general structure:

Aryl includes one or more C1-C20 alkyl moieties covalently bonded to one or more C6-C20 aryl moieties. In some embodiments, aryl is of the general structure:

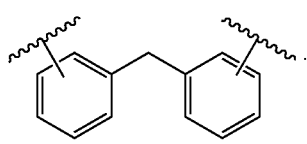

Alkyl includes C1-C20 alkyl, such as C1-C6 alkyl. Alkyl may be of the structure:

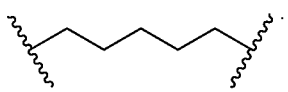 [SMILES: *CCCCC*]

Subsequent reaction of the α-terminus (—NH$_2$) and/or ω-terminus (—NH$_2$) of the diamine-acceptor adduct with additional acceptors and additional diamines forms a poly (amine-imide) oligomer. The poly(amine-imide) oligomer may further react with additional acceptors and additional diamines to form a poly(amine-imide) copolymer. For example, each of the α- and ω-termini of a diamine may react with an acceptor, such as a diacrylate or a maleimide of general structure (1), to form a poly(amine-imide) copolymer, as shown in Scheme 2.

Scheme 2

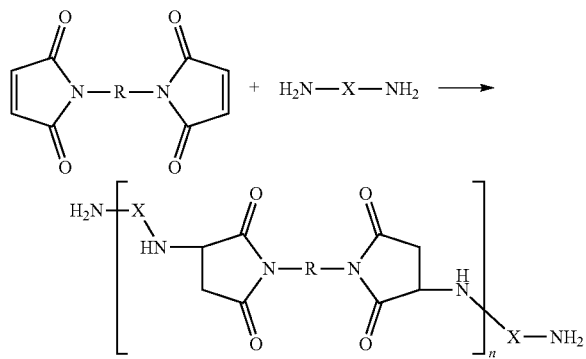

'X' is as described for the diamine of Scheme 1. 'R' is as described for the maleimide of general structure (1). Furthermore, the α-terminus (—NH$_2$) and/or ω-terminus (—NH$_2$) of a poly(amine-imide) oligomer or copolymer may react with paraformaldehyde to form an imine capable of forming a hexahydrotriazine linkage in the reaction mixture to yield a copolymer. Other oligomers and polymers described herein having —NH$_2$ moieties at the α- and/or ω-termini may also react at the α- and/or ω-termini with an acceptor monomer, oligomer, or polymer.

In some embodiments, maleimides described herein are formed in situ by reacting an anhydride with an amine in a reaction mixture. For example, ethylene glycol bis(trimellitic anhydride) and 4,4'-(1,4-phenylenediisopropylidene) bisaniline are added to a reaction mixture to form a polyimide. Furthermore, an anhydride may also self-polymerize to form a polyanhyride upon curing.

In some embodiments, an acceptor, such as a diacrylate or a maleimide of general structure (1), self-polymerizes, such as by radical self-polymerization, to form a self-polymerized acceptor. Self-polymerization of a maleimide of general structure (1), for example, yields a polyimide of general structure

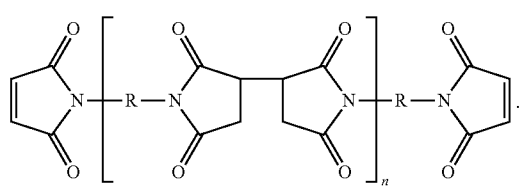

In some embodiments, one or more of the carbon-carbon double bonds at the α,ω-termini of the self-polymerized polyimide may be (1) saturated (e.g., hydrogenated) or (2) unsaturated where the carbon-carbon double bond is an electrophile for subsequent substitution with a diamine monomer, oligomer, or polymer described herein to form a copolymer. In other words, the unsaturated α,ω-termini of a polymerized polyimide may be "acceptor" moieties in that they have an α,β-unsaturated electron withdrawing moiety.

In some embodiments, a reaction mixture comprises one or more cross-linkable polymers, such as linear cross-linkable polymers. As described herein, a cross-linkable polymer includes polymers having (1) a backbone comprising aryl moieties and (2) reactive moieties at the α,ω-termini and, in some embodiments, reactive moieties along the polymer backbone. The reactive moieties at the α,ω-termini of the one or more cross-linkable polymers may be an acceptor (as described previously), an epoxide, an ethylene, and/or a cyanate. A cross-linkable polymer may react to form a fully or partially cross-linked polymer. A cross-linkable polymer includes general structures (2), (3), and (4):

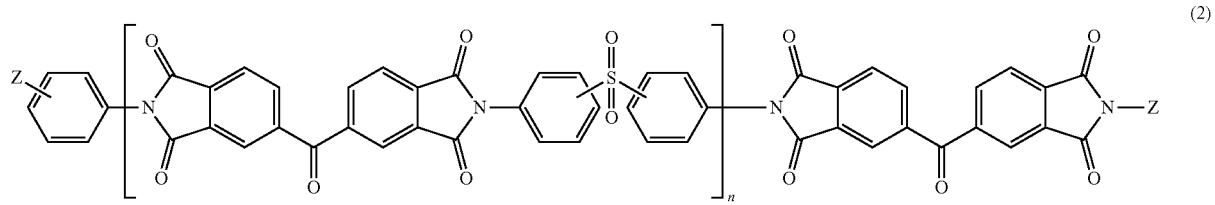

(2)

(3)

-continued

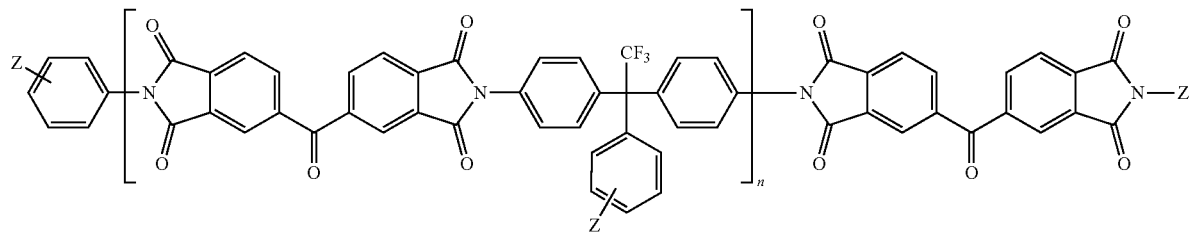

(4)

where each instance of 'Z' is independently selected from a maleimide such as

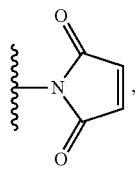

a norbornene-2,3-dicarboximide such as

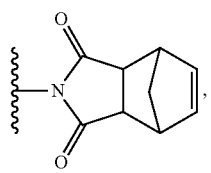 [SMILES: *N1C(=O)C2C3C=CC(C3)C2C1=O]

a cyanate such as

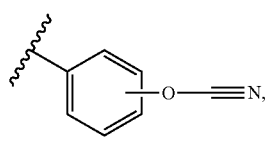

an alkyne such as

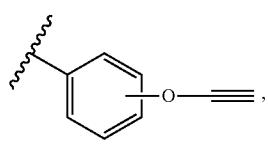

and an epoxide such as

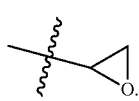 [SMILES: *C1CO1]

In some embodiments, a cross-linkable polymer is an epoxide or is substituted with an epoxide that is a diglycidyl ether, such as a diglycidyl ether of a bisphenol, such as bisphenol A. In embodiments where the one or more cross-linkable polymers is substituted with a maleimide or norbornene-2,3-dicarboximide, the maleimide and norbornene-2,3-dicarboximide can each be an acceptor where the carbon-carbon double bond is an electrophile for substitution with a diamine, such as the diamines shown in Scheme 2, diamine oligomers, or diamine polymers, to form a fully or partially cross-linked copolymer. Alternatively or in addition, the maleimide and norbornene-2,3-dicarboximide may self-polymerize with other cross-linkable polymers substituted with maleimide or norbornene-2,3-dicarboximide, respectively, to form self-polymerized cross-linked polymers that are each a self-polymerized polyimide.

In embodiments where the one or more cross-linkable polymers is substituted with an epoxide, the epoxide may be an electrophile for substitution with a diamine, such as the diamines shown in Scheme 2, diamine oligomers, and/or diamine polymers to form a poly(aminoalcohol) polymer.

In embodiments where the one or more cross-linkable polymers is substituted with a cyanate or alkyne, the cyanate and alkyne allow self-polymerization to form self-polymerized cross-linked polymers. Self-polymerization of cyanates and alkynes does not interact with other PHT network forming reactions in a reaction mixture, e.g. the reactions with diamine monomers, diamine oligomers, and/or diamine polymers. Self-polymerization of cyanates and/or alkynes in a reaction mixture containing one or more of other reaction products (e.g. reactions with diamines) yields a product blend where the morphology is controlled by kinetic quenching of the reactions occurring of a reaction mixture. PHT network forming reactions that do not interact with other PHT network forming reactions allows for a systems chemistry approach to polymer product formation where the reaction mixture forms a product that becomes increasingly viscous as the two or more reactions are occurring in the reaction mixture/product to a point where viscosity is such that further reactions with monomers, oligomers, and/or polymers are kinetically quenched, i.e. subsequent reaction of monomers, oligomers, and polymers in the reaction mixture/product substantially or completely terminates. Kinetic quenching of a reaction mixture allows for reduced biphasic separation of a multicomponent product.

Furthermore, co-polymerization and/or self-polymerization of a reaction mixture can be tuned by a cure temperature of a reaction mixture and volume fraction of the starting materials in the reaction mixture to enable further control of the properties of a resulting product. For example, a cure temperature may be such that a first co-polymerization and/or a first self-polymerization occur in a single vessel and the viscosity of a resulting product increases (vitrification) as the reactions progress, resulting in substantial or complete termination of further co-polymerization and/or self-polymerization. In some embodiments, curing at a temperature above about 150° C., such as between about 200° C. and about 250° C., such as about 175° C., promotes self-polymerization of a conjugated molecule, such as an acceptor. Curing temperatures above 150° C. also promote solvent removal, if a solvent is present. Controlled vitrification of products described herein allows for products, such as thermosets, with decreased storage modulus (G') as compared to a thermoset containing exclusively PHT polymers. Controlled vitrification of thermosets described herein further allows for products that exhibit specific melt and or glass transitions (such as above 150° C., such as between about 190° C. and about 210° C.).

In some embodiments, products may be applied to a substrate, such as a metal screen, by dipping a substrate into a solution containing starting materials followed by curing. Products may also be applied to a substrate by spray-coating a substrate with a solution containing starting materials followed by curing. Curing temperatures may be between about 50° C. and about 250° C., such as about 150° C. and about 225° C., for example 200° C. Curing promotes polymer formation and dispersal of starting materials in an increasingly vitrified product. In some embodiments, a diamine is present in a reaction mixture from about 1 v/v % to about 99 v/v %, about 10 volume % (v/v %) to about 90 v/v %, such as about 25 v/v % to about 75 v/v %, such as about 40 v/v % to about 60 v/v %. In some embodiments, a Michael acceptor is present in a reaction mixture from about 1 v/v % to about 99 v/v %, about 10 volume % (v/v %) to about 90 v/v %, such as about 25 v/v % to about 75 v/v %, such as about 40 v/v % to about 60 v/v %. In some embodiments, a cross-linkable polymer is present in a reaction mixture from about 1 v/v % to about 99 v/v %, about 10 volume % (v/v %) to about 90 v/v %, such as about 25 v/v % to about 75 v/v %, such as about 40 v/v % to about 60 v/v %.

EXAMPLES

Tg values were determined by differential scanning calorimetry (DSC). Total heat flow may be separated into reversing and nonreversing components. The reversing signal contains heat capacity related events such as the glass transition and may be expressed as "reversing heat capacity" (Rev Cp). DSC analyses were performed on a TA Instruments Q2000. The samples (5 to 7 mg) were scanned from −80° C. to 250° C. at a 5° C./min heating rate in aluminum closed pans.

Example 1

0.2 g ODA (1 mmol), 0.057 g paraformaldehyde (1.9 mmol, 1.9 eq.), 0.1 g 1,1'-(methylenedi-4,1-phenylene)bismaleimide (0.28 mmol, 0.28 equiv.) and 1.5 mL N-methyl pyrrolidone (final weight concentration=0.24 g/mL) were weighted out in a 3-dram vial equipped with a stir bar. The vial was capped and transferred into a 50° C. sand bath. After approx. 15 min, the solution became clear. After another 3 h, the solution was deposited on a glass microscope slide with aluminum tape (80 μm thickness) boundaries using a glass pasteur pipet. The following thermal treatment was used: 50° C. for 1 h, 50° C. to 110° C. over 1 h, 110° C. for 1 h, 110° C. to 200° C. over 1 h, 200° C. for 1 h after which the film was allowed to cool down to room temperature. The aluminum tape was carefully peeled off the slide and the film was floated from the glass plate by soaking in deionized water. The film was next rinsed with acetone and dried in a vacuum oven overnight. TGA: $T_5\%$=245° C. DSC: $T_g$=186° C.

FIG. 1 is a graph, hereinafter referred to as "Graph 1", illustrating relative glass transitions (reversing heat capacity) obtained after curing the films at 200° C. Percentages of maleimide are weight % of maleimide starting material relative to weight % ODA in a starting composition before curing. Amounts of paraformaldehyde are adjusted relative to initial amounts of maleimide/ODA.

As shown in Graph 1, each film has a single Tg and each Tg is between the Tg of the pure ODA/bismaleimide resin (Tg=210° C. at "100%") and the pure ODA/paraformaldehyde PHT resin (Tg=190° C., not shown). Therefore, the bismaleimide/ODA (with self-polymerized bismaleimide) and ODA/paraformaldehyde resins are intimately mixed and the Tg of the overall material can be adjusted by adjusting the initial ratio of reagents.

Example 2

0.2 g ODA (1 mmol), 0.056 g paraformaldehyde (1.9 mmol, 1.9 eq), 0.1 g diglycidyl ether of bisphenol A (0.3 mmol, 0.28 equiv.) and 1.5 mL N-methyl pyrrolidone (final weight concentration=0.24 g/mL) were weighted out in a 3-dram vial equipped with a stir bar. The vial was capped and transferred into a 50° C. sand bath. After approx. 15 min, the solution became clear. After another 5 min, the solution was deposited on a glass microscope slide with aluminum tape (80 μm thickness) boundaries using a glass pasteur pipet. The following thermal treatment was used: 50° C. for 1 h, 50° C. to 110° C. over 1 h, 110° C. for 1 h, 110° C. to 200° C. over 1 h, 200° C. for 1 h after which the film was allowed to cool to room temperature. The film couldn't be peeled off by floating technique in deionized water and had to be scraped off of slide using a razor blade. TGA: T5%=280° C. DSC: Tg=147° C.

Example 3

0.2 g ODA (1 mmol), 0.1 g paraformaldehyde (3.3 mmol, 3.3 eq), 0.1 g polyimide of ethylene glycol bis(trimellitic anhydride) and 4,4'-(1,4-phenylenediisopropylidene)bisaniline (approx. 5 mmol) and 1.6 mL N-methyl pyrrolidone (final weight concentration=0.25 g/mL) were weighted out in a 3-dram vial equipped with a stir bar. The vial was capped and transferred into a 50° C. sand bath. After 1 h, the solution was filtered through a 0.2 mm glass fibers filter and deposited on a glass microscope slide with aluminum tape (80 μm thickness) boundaries using a glass pasteur pipet. The following thermal treatment was used: 50° C. for 1 h, 50° C. to 110° C. over 1 h, 110° C. for 1 h, 110° C. to 200° C. over 1 h, 200° C. for 1 h after which the film was allowed to cool to room temperature. The aluminum tape was carefully peeled off the slide and the film was floated from the glass plate by soaking in deionized water. The film was next rinsed with acetone and dried in a vacuum oven overnight. TGA: T5%=253° C. DSC: Tg=157° C.

Figure 2:
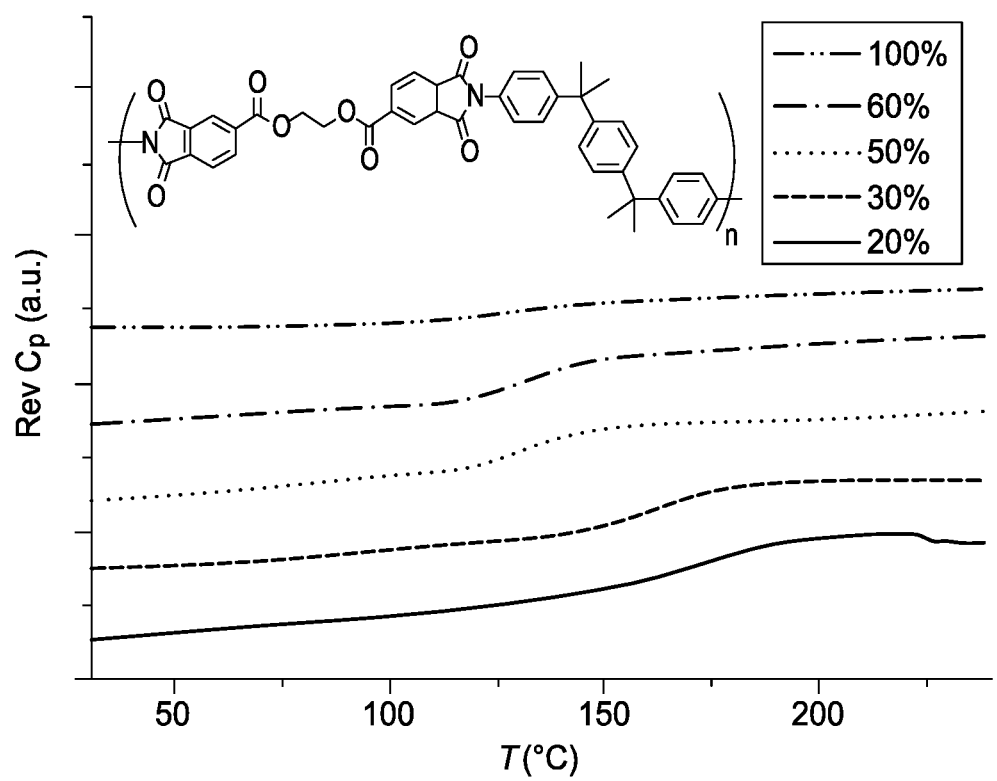
FIG. 2 is a graph illustrating relative glass transitions (reversing heat capacity) obtained after curing the films at 200° C.

FIG. 2 is a graph, herein after referred to as "Graph 2", illustrating relative glass transitions (reversing heat capacity) obtained after curing the films at 200° C. Percentages shown are weight % of (ethylene glycol bis(trimellitic anhydride+4,4'-(1,4-phenylenediisopropylidene)bisaniline) relative to weight % ODA in a starting composition before curing. Amounts of paraformaldehyde are adjusted relative to initial amounts of ODA/(ethylene glycol bis(trimellitic anhydride 4,4'-(1,4-phenylenediisopropylidene)bisaniline).

As shown in Graph 2, each film has a single Tg and each Tg is between the Tg of the pure ODA/(ethylene glycol bis(trimellitic anhydride+4,4'-(1,4-phenylenediisopropylidene)bisaniline) resin (Tg=210° C. at "100%") and the pure ODA/paraformaldehyde PHT resin (Tg=190° C., not shown). Therefore, the ODA/(ethylene glycol bis(trimellitic anhydride+4,4'-(1,4-phenylenediisopropylidene)bisaniline) (with self-polymerized bismaleimide) and ODA/paraformaldehyde resins are intimately mixed and the Tg of the overall material can be adjusted by adjusting the initial ratio of reagents.

Overall, a systems chemistry approach may be used to synthesize PHT products that achieve tunable material properties such as yield strength, char yield, and thermal response. A systems chemistry approach further allows the combination of two materials with different properties in order to prepare a single material with the properties of its two constituting components in a reactive blending approach. A systems chemistry approach allows for access to tunable properties through the directed application of isolated chemical reactions, simultaneously in a single vessel. A systems chemistry approach allows mitigation of some of the challenges for recyclable high-performance hexahydrotriazines conveniently by incorporating functional groups that have the desired material properties in a single step through judicious choice of polymers and/or co-polymers based on reactivity. For example, self-polymerization of cyanates and/or alkynes in a reaction mixture containing one or more of other reaction products (e.g. reactions with diamines) yields a product blend where the morphology is controlled by kinetic quenching of the reactions occurring in a reaction mixture. Kinetic quenching of a reaction mixture allows for reduced biphasic separation of a product. Furthermore, co-polymerization and/or self-polymerization of a reaction mixture can be tuned by a cure temperature of a reaction mixture and volume fraction of the starting materials in the reaction mixture to enable further control of the properties of a resulting product.

The present disclosure has been presented for purposes of illustration and description, but is not intended to be exhaustive or limited to the embodiments in the form disclosed. Many modifications and variations will be apparent to those of ordinary skill in the art without departing from the scope and spirit of the embodiments. The embodiments were chosen and described in order to best explain the principles of the embodiments and their practical application, and to enable others of ordinary skill in the art to understand the embodiments.

What is claimed is:
1. A product that is the reaction product of:
   a first compound that is a diamine;
   a second compound that is an aldehyde;
   a third compound having an α,β-unsaturated electron withdrawing moiety; and
   a fourth compound that is a cross-linkable polymer.
2. The product of claim 1, wherein the aldehyde is paraformaldehyde.
3. The product of claim 1, wherein the cross-linkable polymer is functionalized with at least one of cyanate, alkyne, epoxide, maleimide, or norbornene-2,3-dicarboximide.
4. The product of claim 1, wherein the cross-linkable polymer is selected from the group consisting of:

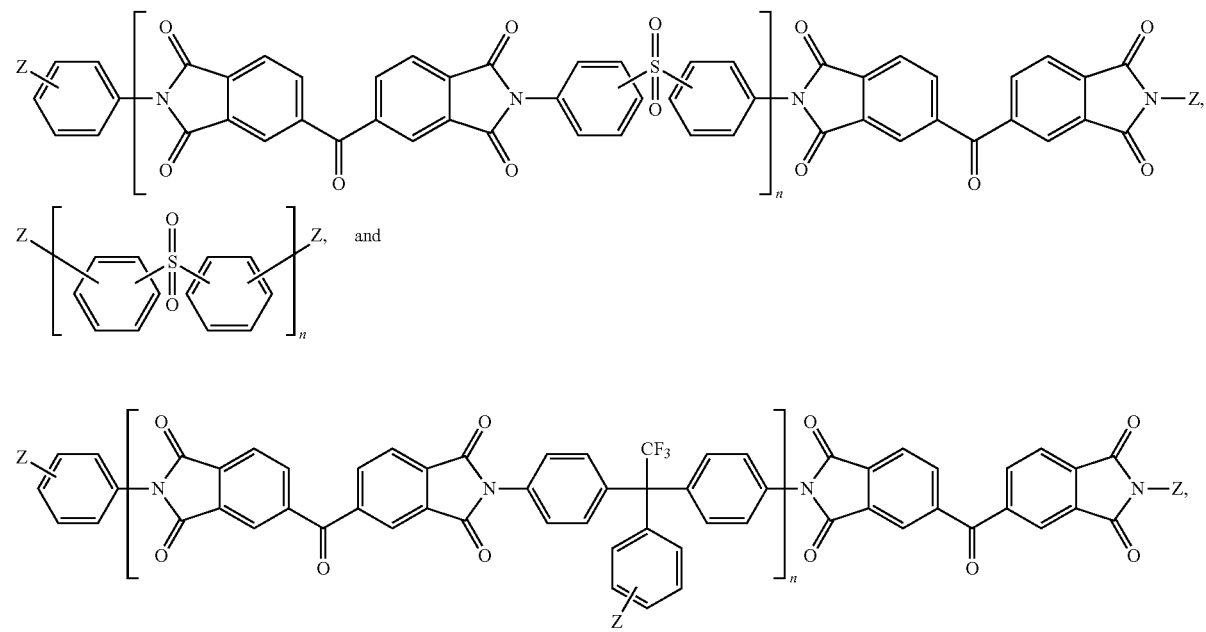

wherein each instance of CZ' is independently selected from a maleimide group, a norbornene-2,3-dicarboximide, a cyanate, an alkyne, and an epoxide, wherein the maleimide group, the norbornene-2,3-dicarboximide, the cyanate, the alkyne, and the epoxide are unsubstituted or substituted with alkyl or aryl, and wherein n is a positive integer.
5. The product of claim 4, wherein the maleimide is

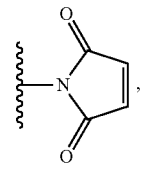 [SMILES: *N1C(=O)C=CC1=O]

the norbornene-2,3-dicarboximide is

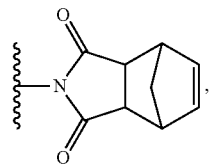 [SMILES: *N1C(=O)C2C3C=CC(C3)C2C1=O]

the cyanate is

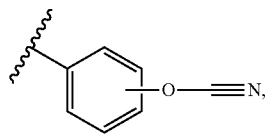

the alkyne is

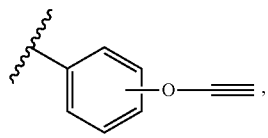

and the epoxide is

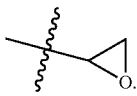

6. The product of claim 1, wherein the compound having an α,β-unsaturated electron withdrawing moiety is

wherein R is selected from the group consisting of ether, aryl, and alkyl.

7. The product of claim 6, wherein the ether is the aryl is

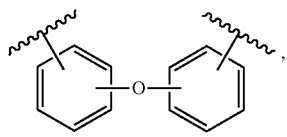

and the

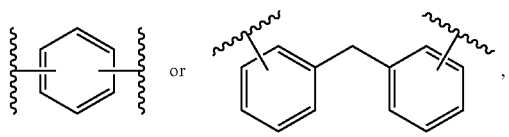

alkyl is

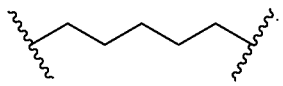 [SMILES: *CCCCC*]

8. The product of claim 6, wherein R is an ether.
9. The product of claim 6, wherein R is aryl.
10. The product of claim 6, wherein R is alkyl.
11. The product of claim 1, wherein the diamine is of the structure: $NH_2$—X—$NH_2$, wherein X is selected from the group consisting of a phosphine derivative, an ether, and a lactone.
12. The product of claim 11, wherein the phosphine derivative is

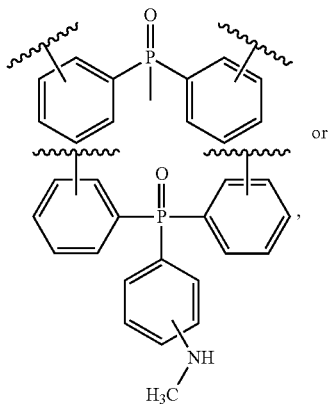

the ether is

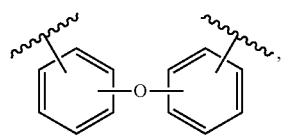

and the lactone is

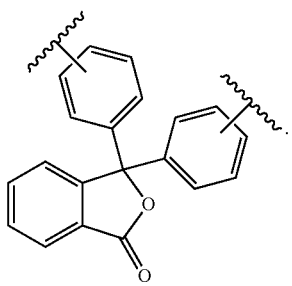

13. The product of claim 1, wherein the compound having an α,β-unsaturated electron withdrawing moiety is an acrylate that is 1,4-butanediol diacrylate or trimethylolpropane triacrylate.

14. The product of claim 1, wherein the cross-linkable polymer is an epoxide that is a diglycidyl ether of a bisphenol.

15. The product of claim 1, wherein the cross-linkable polymer is a compound with a backbone comprising aryl moieties.

16. The product of claim 1, wherein the cross-linkable polymer is a compound comprising one or more functional moieties present at an α-terminus, a ω-terminus, and/or along a polymer backbone of the cross-linkable polymer.

* * * * *